(12) United States Patent
Smith et al.

(10) Patent No.: US 9,943,558 B2
(45) Date of Patent: Apr. 17, 2018

(54) COMPOSITIONS AND METHODS FOR TREATING MULTI-DRUG RESISTANT MALARIA

(75) Inventors: Garth Selwyn Smith, Guilin (CN); Lixin Zhang, Beijing (CN); Huanqin Dai, Beijing (CN)

(73) Assignee: Febris Bio-Tech Limited, Whitianga (NZ)

( * ) Notice: Subject to any disclaimer, the term of this patent is extended or adjusted under 35 U.S.C. 154(b) by 496 days.

(21) Appl. No.: 14/005,721

(22) PCT Filed: Sep. 10, 2011

(86) PCT No.: PCT/IB2011/053962
§ 371 (c)(1),
(2), (4) Date: Nov. 26, 2013

(87) PCT Pub. No.: WO2012/127287
PCT Pub. Date: Sep. 27, 2012

(65) Prior Publication Data
US 2014/0072663 A1 Mar. 13, 2014

Related U.S. Application Data

(60) Provisional application No. 61/454,246, filed on Mar. 18, 2011.

(51) Int. Cl.
| | |
|---|---|
| *A61K 36/28* | (2006.01) |
| *A61K 36/42* | (2006.01) |
| *A61K 36/185* | (2006.01) |
| *A61K 31/365* | (2006.01) |
| *A61K 31/385* | (2006.01) |
| *A61K 31/704* | (2006.01) |
| *A61K 31/366* | (2006.01) |
| *A61K 36/18* | (2006.01) |

(52) U.S. Cl.
CPC ............ *A61K 36/28* (2013.01); *A61K 31/365* (2013.01); *A61K 31/366* (2013.01); *A61K 31/385* (2013.01); *A61K 31/704* (2013.01); *A61K 36/18* (2013.01); *A61K 36/42* (2013.01)

(58) Field of Classification Search
None
See application file for complete search history.

(56) References Cited

U.S. PATENT DOCUMENTS

| | | | | |
|---|---|---|---|---|
| 7,122,198 B1 * | 10/2006 | Singh | ................... | A61K 9/0056 424/401 |
| 8,435,588 B2 * | 5/2013 | Prakash | ................ | A23L 1/2364 426/548 |
| 2009/0053378 A1 * | 2/2009 | Prakash | ................ | A23L 1/236 426/548 |
| 2010/0272838 A1 | 10/2010 | Prendergast | | |

FOREIGN PATENT DOCUMENTS

| | | | |
|---|---|---|---|
| CN | 1771936 A | * | 5/2006 |
| EP | 2215914 A1 | | 8/2010 |
| WO | 0156959 A1 | | 8/2001 |
| WO | 2007061912 A2 | | 5/2007 |
| WO | 2009126950 A2 | | 10/2009 |
| WO | 2010056223 A1 | | 5/2010 |

OTHER PUBLICATIONS

Australian Government, IP Australia, Patent Examination Report No. 1 for the corresponding Australia Patent Application No. 2011363456 dated Jun. 10, 2015.
New Zealand Intellectual Property Office, Further Examination Report for the corresponding New Zealand Patent Application IP No. 615437 dated May 29, 2015.
European Patent Office, Communication pursuant to Article 94(3) EPC for the corresponding European Patent Application No. 11 861 334.8 dated Jun. 29, 2015.
New Zealand Intellectual Property Office, First Examination Report for the corresponding IP No. 615437 dated May 21, 2014.
Australian Government, IP Australia, Notification of Material Filed Under Section 27 for the corresponding Australia Patent Application No. 2011363456 dated Oct. 27, 2014.
European Patent Office, Search Report for the corresponding European Patent Application No. 11 861 334.8 dated Nov. 18, 2014.
Kalauni, S., et al. Antimalarial activity of cassane- and norcassane-type diterpenes from Caesalpinia crista and their structure-activity relationship. Biological and Pharmaceutical Bulletin, 29(5): 1050-2, May 26, 2006. (Document B).
Suksamran, S., et al., Ceanothane- and lupane-type triterpenes with antiplasmodial and antimycobacterial activities from Ziziphus cambodiana. Chemical and Pharmaceutical Bulletin, 54(4): 535-7, May 1, 2006. (Document C).
Kirandeep, K., Meenakshi, J., Tarandeep, K., & Rahul, J. (2009). Antimalarials from nature. Bioorganic & Medicinal Chemistry, 17(9):3229-56, May 1, 2009. (Document D).

\* cited by examiner

*Primary Examiner* — Chris R Tate
*Assistant Examiner* — Randall Winston
(74) *Attorney, Agent, or Firm* — Brooks Kushman P.C.

(57) ABSTRACT

A method is provided for treating an individual for a malarial infection, in particular drug-resistant species of *Plasmodium*, including administering to the individual in need of such treatment a composition comprising an extract containing an effective amount of one or more anti-malarial di- or tri-terpene compounds. Potent and effective extracts containing the anti-malarial compounds can be derived from Luo Han fruit and *Stevia* leaves, including combinations of the same, for the purpose of treating and preventing malaria in an inexpensive manner from readily available commodities. In one embodiment, the composition is administered orally in a solid or liquid ingestible form.

9 Claims, 3 Drawing Sheets

COMPOSITIONS AND METHODS FOR TREATING MULTI-DRUG RESISTANT MALARIA

FIELD OF THE INVENTION

A method for treating an individual for a malarial infection is described. In particular, a method for treating an individual infected with a malarial drug-resistant species of *Plasmodium*, including administering to the individual in need of such treatment a composition containing one or more di- or tri-terpene compounds is disclosed. Potent and effective compounds derived from the fruit of *Siraitia grosvenorii* (Luo Han Guo) and the leaves of *Stevia* (*Stevia rebaudiana*), including combinations of the same, have been found to contain effective amounts of the di or tri-terpene compounds and these are described. In one embodiment, the inventive composition is administered orally in a solid or liquid ingestible form.

BACKGROUND

Malaria is a devastating infectious disease, and each year 350-500 million cases occur worldwide. As a major health concern in Asia, Africa, the Middle East, and Central and South America, about 41% of the world's population live in areas where malaria is transmitted. And still more tragically, malaria causes 11% of all children's deaths in developing countries. For example, the World Health Organization (WHO) reported that in 2008, malaria caused nearly one million deaths, mostly among African children. In Africa, a child dies every 45 seconds of malaria, and the disease accounts for 20% of all childhood deaths.

Antimalarial treatments, primarily drug therapies, are known. The quinines (or quinoline class), e.g. chloroquine, mefloquine, are well known as therapeutic agents. Other drug combinations have been developed as well. The best currently available treatment, particularly for *P. falciparum* malaria, is artemisinin-based combination therapy ("ACT"). Artemisinin is derived from a plant, *Artemisia annua*, which belongs to the Asteraceae family.

Unfortunately, two fundamental problems have arisen in the fight against malaria, namely, drug resistance and the high cost of drugs and medical treatments. There clearly exists an urgent need for alternative therapies that avoid the development of drug resistance by *Plasmodium*, and drastically lower the costs associated with treating malaria. It would be a contribution to the art of medicine to provide a readily available, easily accessible antimalarial composition administrable in various forms.

According to WHO data, if resistance to artemisinins develops and spreads to other large geographical areas, as has happened before with chloroquine and sulfacoxine-pyrimethamine (SP), the public health consequences could be dire, as it is possible that no alternative antimalarial medicines will be available in the near future.

Furthermore, assuming that the same concentration of the extract from the fruit of Luo Han containing the composition of the present invention is as effective as that of artemisinin derivatives, the cost of the Luo Han extract would be only a fraction of the cost per artemisinin treatment to cure malaria. The same could be said of *Stevia* leaf-based extracts. Even if a substantially greater amount of the active ingredients derived from Luo Han and/or *Stevia* were required for antimalarial treatments, the cost savings compared to currently marketed therapies would be immense.

Certain di- and tri-terpene glycosides are known as sweeteners, but there have been no reports of using such compounds for treatment of malaria in a human subject.

It would be a further contribution to the art of medicine to provide a method of treating malaria by administering a composition containing one or more di- or tri-terpene compounds to a human patient in need of such treatment. It would be a further contribution to the art to provide a method of treating drug-resistant malaria by administering to a human patient in need of such treatment an effective amount of the composition of the invention in the form of an extract containing one or more di- or tri-terpene compounds.

SUMMARY OF THE INVENTION

Potent and effective active compounds derived from the fruit of *Siraitia grosvenorii* (Luo Han Guo) and the leaves of *Stevia* (*Stevia rebaudiana*), including combinations of the same, have been found to contain effective amounts of one or more di- or tri-terpenes. These potent compounds including mogrosides can be extracted from Luo Han fruit. In one embodiment, assuming that the same concentration of the extract from Luo Han is generally as effective as that of artemisinin derivatives, then the cost of the Luo Han extract would be only a fraction of the cost per treatment to cure malaria. Other potent compounds including rebaudioside A can be extracted from *Stevia* leaves.

A method of treating an individual for a malarial infection is provided, comprising administering to the individual in need of such treatment a therapeutically effective amount of a composition comprising a *Stevia* leaf extract containing steviol glycosides and an acceptable carrier.

In a further embodiment, a Luo Han fruit extract can be included in a composition for treatment of malaria. Further, a method of treating an individual for a malarial infection is provided, comprising administering to the individual in need of such treatment a therapeutically effective amount of a composition comprising a Luo Han fruit extract and an acceptable carrier.

In an alternative embodiment, a method of treating an individual for a malarial infection is provided, comprising administering to the individual in need of such treatment a therapeutically effective amount of a composition comprising at least one of a di-terpene or a tri-terpene, and an acceptable carrier.

In an alternative embodiment, a method of treating an individual for a malarial infection is provided, comprising administering to the individual in need of such treatment a therapeutically effective amount of a composition comprising rebaudioside A, a Luo Han fruit extract, and an acceptable carrier.

In yet another embodiment, a method of treating an individual for a malarial infection is provided, comprising administering to the individual in need of such treatment a therapeutically effective amount of a composition comprising at least one of a di-terpene or a tri-terpene, in combination with one or more antimalarial compounds selected from the group consisting of mefloquine, halofantrine, artesunate, artemether, chloroquine, lumefantrine, primaquine, sulfadoxine, sulfalene, pyrimethamine, doxycycline, tetracycline, azithromycine, proguanil, cycloguanil, dapsone, artemsinin and atovoquone, but preferably artemsinin.

In yet another embodiment, an antimalarial composition comprising a therapeutically effective amount of rebaudioside A, a therapeutically effective amount of a Luo Han fruit extract, and an acceptable carrier is provided. The antimalarial composition can further include a therapeutically effective amount of a compound selected from the group consisting of mefloquine, halofantrine, artesunate, artemether, chloroquine, lumefantrine, primaquine, sulfadoxine, sulfalene, pyrimethamine, doxycycline, tetracycline, azithromycine, proguanil, cycloguanil, dapsone, artemsinin, atovoquone, and combinations thereof.

DETAILED DESCRIPTION

The potent and effective di- and tri-terpenes disclosed herein may be contained in a composition for the safe treatment of malarial infections. The potent and effective di- and/or tri-terpene active compounds including mogrosides can be extracted from Luo Han fruit. The potent and effective di- and/or tri-terpene active compounds including rebaudioside A can be extracted from *Stevia* leaves. Alternatively or additionally, such di- and/or tri-terpene compounds, including mogrosides and/or rebaudioside A, can be extracted or isolated from any suitable natural or botanical source.

In an alternative embodiment, the composition containing one or more di- or tri-terpene compounds for the treatment of malarial infections can further include a sesquiterpene lactone, e.g. artemisinin.

Preferably, the composition contains ingredients that are considered to be safe and effective for human consumption and use.

The term "effective amount" as used herein means an amount or concentration of a compound according to the present invention which is effective within the context of its administration or use, which may be inhibitory, prophylactic and/or therapeutic. In general, it is preferable to administer the composition in an orally-administrable form, but certain formulations may be administered via a parenteral, intravenous, intramuscular, transdermal, buccal, subcutaneous, suppository or other route.

Malarial infections are caused by *Plasmodium* parasites. The parasites are spread to people through infected Anopheles mosquitoes, called "malaria vectors".

There are four types of human malaria: *Plasmodium falciparum, Plasmodium vivax, Plasmodium ovale,* and *Plasmodium malariae*. According to the WHO, in recent years, some human cases of malaria have also occurred with *Plasmodium knowlesi*—a malaria affecting monkeys, that occurs in certain forested areas of Southeast Asia.

Terpenes comprise a broad class of natural botanical materials. Monoterpenes include two isoprene units and have the general formula $C_{10}H_{16}$. Terpenes can be acyclic or cyclic, although most bioactive species include one or more rings, which can be fused or bridged. Sesquiterpenes possess three isoprene units and include artemisinin and derivatives thereof, a known class of peroxy-bridged lactone. Di-terpenes, which are composed of four isoprene units, encompass a broader group of biologically important compounds which includes steviol, forskolin, and the like. Finally, tri-terpenes, which are composed of six isoprene units, represent an even broader group of compounds generally having a $C_{30}$ carbon skeleton or core structure. Squalene, and other biological steroids, arise from this class, as do the cucurbitane-related compounds. Tri-terpenes comprise a class of compounds that are numerous and widely distributed in nature, occurring principally in plants. Cucurbitanes are tri-terpenes that are found in many plants, and some of these compounds, such as cucurbitacins, mogrosides I-VI, momordicins, and the like, are important phytochemicals.

Di-terpenes and tri-terpenes, and their derivatives, including glycoside derivatives, which are contemplated as useful for the present antimalarial compositions, include, but are not limited to: rebaudioside A, rebaudioside B, rebaudioside C, rebaudioside D, rebaudioside E, rebaudioside F, dulcoside A, dulcoside B, rubusoside, stevioside, steviolbioside, mogroside II, mogroside III, mogroside IV, mogroside V, siamenoside I, grosmomoside I, and combinations thereof. Further, as appropriate, use of salts, solvates, and prodrugs of these ingredients is also contemplated.

Steviol glycosides are contained in purified extracts from the leaves of the South American herb *Stevia rebaudiana*. Currently, *Stevia* is cultivated and used in food in many places around the world. Rebaudioside A (often referred to as "rebianna" or "Reb A") and stevioside are the dominant components of the extracts, and both are di-terpenes. Reb A is named (14α)-13-[(2-O-β-D-glucopyranosyl-3-O-β-D-glucopyranosyl-β-D-glucopyranosyl)oxy]kaur-16-en-19-oic acid β-D-glucopyranosyl ester. The structure of Reb A is depicted in the compound of formula (1):

(1)

Stevioside possesses one less glucosyl group at the C-13 position, specifically, lacking the 3-O-glucopyranosyl group of Reb A.

Both Reb A and stevioside are known to be non-nutritive sweeteners, at comparative levels of about 300 times as sweet as sucrose, and 350-450 times as sweet as sucrose, respectively. At present, steviol glycosides are used primarily as non-calorie sweeteners and flavor enhancers.

Rebaudioside A has been granted GRAS (Generally Regarded as Safe) notification status from the U.S. Food and Drug Administration (numbers 252 and 253).

In human metabolic studies, both stevioside and Reb A are converted to steviol, which then conjugates to glucuronic acid to form steviol glucuronide, and is excreted in the urine during Phase II metabolism. The half-life ($t_{1/2}$) for both glycosides in humans is approximately 14 hours. In addition, at the dosages used herein, Reb A does not exhibit adverse hemodynamic effects or blood glucose lowering effects. The only reported pharmacological effects of steviol glycosides were observations at very high dose rates (about 750 to 1500 mg/day) of decreased blood pressure and the lowering of blood glucose levels.

A composition containing Reb A, and an acceptable carrier, can be used for the treatment of malarial infections. It is further expected that combinations of the active compounds selected from the group consisting of rebaudioside A, rebaudioside B, rebaudioside C, rebaudioside D, rebaudioside E, rebaudioside F, dulcoside A, dulcoside B, rubusoside, stevioside, and steviolbioside, when formulated with a pharmaceutically acceptable carrier, would be therapeutically effective for treatment of malaria in a human patient, including drug resistant infections of *Plasmodium* spp.

Luo Han fruit (Chinese, luo han guo), or monk fruit, are produced by a plant (*Siraitia grosvenorii*), which only grows in the northern parts of Guangxi province, in southern China. The plant is a perennial vine in the Cucurbitaceae (cucumber or melon) family. This fruit is widely used as a dietary and medicinal food throughout China and Southeast Asia, and has been cultivated for such uses for centuries. In China, the fruits are frequently used as the main ingredient in "cooling drinks or tea." Traditionally, the fruit was used to make a decoction with hot water and drunk for the treatment of throat and lung ailments. Additionally, the juice of Luo Han fruit is very sweet, and some of the components of Luo Han fruit have been used as sweeteners.

Extracts of Luo Han fruit are described herein. The primary components of the Luo Han fruit extracts are cucurbitane tri-terpene glycosides known as mogrosides, specifically mogrosides II, III, IV, V, and VI, along with flavonoids and melanoidins. The sweet taste of Luo Han fruit is derived mainly from mogrosides, esp. mogroside V, which comprise a group of tri-terpene glycosides that constitute approx. 0.5% to 1% by weight of the dried fruit. Mogroside V has been identified as the major terpenoid component and principal glycoside component, and using extraction and other isolation means can be obtained at levels of about 30-60% by weight, for example. Furthermore, Luo Han fruit extracts can contain >45% by weight up to about 48% by weight total mogrosides including mogroside derivatives and/or metabolites. Mogroside V is named (3β,9β,10α,11α,24R)-3-[(6-O-β-D-glucopyranosyl-β-D-glucopyranosyl)oxy]-11,25-dihydroxy-9-methyl-19-nor-lanost-5-en-24-yl-O-β-D-glucopyranosyl-(1-2)-O-[β-D-glucopyranosyl-(1-6)]-β-D-glucopyranoside. The structure of mogroside V is depicted in the compound of formula (2):

(2)

The mogrosides are known to be non-nutritive sweeteners, and mogroside V is up to 300 times as sweet as sugar in its pure form.

One useful Luo Han fruit extract containing Mogroside V has been granted GRAS (Generally Regarded as Safe) notification status from the U.S. Food and Drug Administration (number 301).

An example of a mogroside derivative or metabolite is 11-oxo-mogroside V, which can also be present in substantial amounts in the Luo Han fruit extracts described herein, up to about 8% by weight.

It is further expected that a Luo Han fruit extract, when formulated with a pharmaceutically acceptable carrier, would be therapeutically effective for treatment of malaria in a human patient, including drug resistant infections of *Plasmodium* spp.

*Artemisinin* is extracted and isolated from *Artemisia annua* (a small shrub belonging to the Asteraceae family and found in temperate Asia; commonly known as sweet worm wood). Other artemisinin derivatives useful for embodiments disclosed herein include, but are not limited to, artemether, arteether, dihydroartemisinin, artesunate, and the like. As discussed above, one major focus of medicinal research into malaria is artemisinin-based combination therapies ("ACT"). These therapies combine artemisinin derivatives with companion drugs. For example, one well known combination includes artemether and lumefantrine in a 1:6 wt/wt ratio (a.k.a. co-artemether). Lumefantrine is (+/−)-2-dibutylamino-1-[2,7-dichloro-9-(4-chlorobenzylidene)-9,11-fluoren-4-yl]ethanol (a.k.a. benflumetol and dl-benflumelol), and may be combined with other ingredients in embodiments of the invention. However, combinations of artemisinin or its derivatives with di- or tri-terpenes have not been reported. In particular, combinations of artemisinin or its derivatives with a di-terpene glycoside and/or a tri-terpene glycoside have not been reported for use in antimalarial treatments.

*Artemisinin* and many of its derivatives are poorly soluble in water, which may lead to problems with absorption into the human body and delayed uptake. In contrast, certain di- and tri-terpene glycosides as disclosed herein are highly water-soluble, and overcome absorption and bioavailability barriers much more easily. For example, both Reb A and mogroside V are fully water soluble and therefore more useful and readily available for antimalarial treatments when contained in the antimalarial compositions of the present invention.

Without being bound by theory, it is believed that certain di-terpene and/or tri-terpene compounds, used in combination with one or more antimalarial compounds selected from mefloquine, halofantrine, artesunate, artemether, chloroquine, lumefantrine, primaquine, sulfadoxine, sulfalene, pyrimethamine, doxycycline, tetracycline, azithromycine, proguanil, cycloguanil, dapsone, artemsinin and atovoquone, most preferably artemisinin or its derivatives, would provide an effective treatment for malaria, thus clearing or inhibiting Plasmodium parasites present in a human patient, in a synergistic manner. It is expected that ACT using di-terpene and/or tri-terpene glycoside derivatives would provide greater therapeutic effects than either agent alone, i.e. artemisinin vs. terpene compound, and also avoid drug resistance. In an alternative embodiment, it is expected that ACT using artemsinin (or a derivative) and a combination of di-terpene and tri-terpene would provide greater therapeutic effects than any of the agents alone, and also avoid drug resistance. In another alternative embodiment, it is further expected that ACT using artemsinin (or a derivative) and a combination of a Stevia leaf extract containing steviol glycosides and a Luo Han fruit extract would provide greater therapeutic effects than any of the agents alone, and also avoid drug resistance. In another alternative embodiment, it is further expected that ACT using artemsinin (or a derivative) and a combination of a Stevia leaf extract containing steviol glycosides and mogroside V would provide greater therapeutic effects than any of the agents alone, and also avoid drug resistance. In another alternative embodiment, it is further expected that ACT using artemsinin (or a derivative) and a combination of a rebaudioside A and mogroside V would provide greater therapeutic effects than any of the agents alone, and also avoid drug resistance. In another alternative embodiment, it is further expected that ACT using artemsinin (or a derivative) and a combination of a rebaudioside A and a Luo Han fruit extract would provide greater therapeutic effects than any of the agents alone, and also avoid drug resistance.

For example, antimalarial compounds can be used in combination with a di-terpene glycoside and/or a tri-terpene glycoside in embodiments of the present invention. Suitable antimalarial compounds include mefloquine, halofantrine, artesunate, artemether, chloroquine, lumefantrine, primaquine, sulfadoxine, sulfalene, pyrimethamine, doxycycline, tetracycline, azithromycine, proguanil, cycloguanil, dapsone, artemsinin and atovoquone, but preferably artemsinin.

The methods described above may be further understood in connection with the following Examples. Steviol glycosides extract can be obtained from EUSTAS (European Stevia Assoc., Huesca, Spain), and Pure Circle, Oak Brook, Ill., USA. Reb A (a Stevia leaf extract) at about 90-95% purity is available as above and from GLG, Vancouver, British Columbia, Canada. Mogroside V (Luo Han fruit pure extract powder) at about 35-60% purity is available as PureLo® from BioVittoria Limited (Hamilton, New Zealand). Luo Han fruit powder is also available as FruitSweetness™ from BioVittoria Limited (Hamilton, New Zealand), and Guilin Layn Natural Ingredients Corp., Guilin, Guangxi, P.R. China.

The following abbreviations are used in the present specification. EtOAc: ethyl acetate; DMSO: dimethyl sulfoxide; MDR: multi-drug resistant; CQ: chloroquine; PBS: phosphate-buffered saline.

Example 1A

Sample No. 1: Rebaudioside A (Stevia leaf pure extract), >95% purity by weight
Sample No. 2: Steviol Glycosides (Stevia leaf pure extract), ca. 95% purity by weight
Sample No. 3: Luo Han Guo fruit pure extract powder containing Mogroside V (ca. 40% by weight)
Sample No. 4: Luo Han Guo juice concentrate (from Fresh Luo Han fruit)
Sample No. 5: Luo Han Guo extract (water phase)
Sample No. 6: Luo Han Guo extract (n-butanol phase)= "Compound B"
Sample No. 7: Luo Han Guo extract (EtOAc phase)= "Compound A"
Sample No. 8: Luo Han Guo general extract (from Dried Luo Han fruit)

As a first step, Luo Han fruit powder (135 mg), i.e. pure extract powder containing Mogroside V (ca. 40% by weight), was reconstituted in water by hot water extraction (3×400 mL), and the combined water extracts were partitioned, first with EtOAc (200 mL, 2×100 mL), and next with n-butanol (200 mL, 2×100 mL), respectively, to yield 3 fractions corresponding to Samples 5-7 above, and the organic solvent was removed by rotary evaporator to yield "Compound A" (EtOAc fraction) and "Compound B" (n-butanol fraction). Compound A and Compound B were tested for antimalarial activity. Sample 5 corresponds to the final water phase after partitioning with EtOAc, followed by n-butanol.

In addition, the Luo Han Guo general extract (Sample 8) was prepared by extraction of dried Luo Han fruit with hot water as in the first step above without further manipulation.

Preparation of active ingredient solutions. Each of the samples listed above was dissolved in DMSO to prepare a stock solution of 0.1 mg/µL.

Example 1B

The Plasmodium falciparum multidrug resistant strain (MDR) 7G8, (obtained from the Malaria Research and Reference Reagent Resource Centre (MR4), Manassas, Va., USA), was in vitro cultured in RMPI 1640 cell culture medium (supplemented with 10% Human Serum) with PCV (packed cell volume) at 5%. The P. falciparum was cell synchronized by adding 5% of D-sorbitol, and synchronized cells were then spread on culture plates after achieving ring form phase, with an initial infection rate of 1% and PCV at 5%.

The DMSO stock solutions for Sample No. 7 ("Compound A") and Sample No. 6 ("Compound B") as above were diluted by culture medium to 2000 µg/ml as the mother solution and diluted by culture medium for gradient concentration in 3 fold serial dilution form in an activity testing assay (active ingredient solutions should be less than 10% of the culture system, and DMSO concentration should be lower than 0.5% to avoid adverse influence on P. falciparum growth). 10 µl active ingredient solution plus 90 µl P. falciparum culture medium were spread on each well. The cell culture was observed under microscope for infection rate by smear examination with the standard Giemsa stain as is well known in the art.

Percent of inhibition=(infection rate of blank control−infection rate of active ingredient-treated or drug-treated group)/infection rate of blank control×100%.

Figure 1:
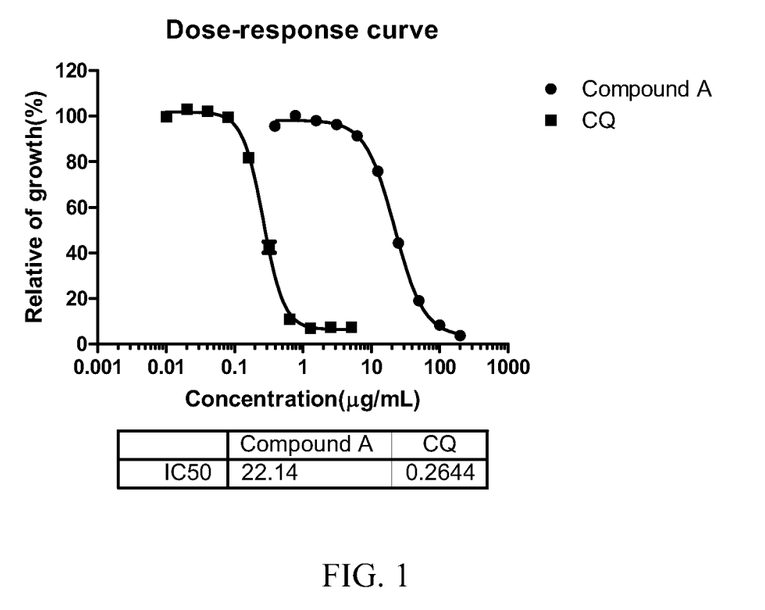
FIG. 1 depicts a dose-response curve (percent of growth vs. active ingredient concentration) describing one embodiment of a Luo Han fruit extract (i.e. the ethyl acetate, EtOAc fraction: "Compound A") used to treat *P. falciparum* 7G8 (a drug-resistant test strain, obtained from the Malaria Research and Reference Reagent Resource Center (MR4), Manassas, Va., USA) in vitro, using chloroquine ("CQ") as a positive control.

Using a chloroquine treated group as positive control, a dose response curve was generated as percent of growth value against active ingredient/drug concentration (Nonlinear Regression Analysis function in software Graphpad Prism 3.0, GraphPad Software, La Jolla, Calif., USA) in order to determine $IC_{50}$ (half maximal inhibitory concentration). FIG. 1 shows dose-response growth inhibition curves for chloroquine (CQ) and Compound A.

TABLE 1

| Sample | Antimalarial activity, $IC_{50}$ (µg/mL) |
| --- | --- |
| CQ (Chloroquine) | 0.264 ± 0.012 |
| 7 (EtOAc fraction of 40% Luo Han fruit powder) "Compound A" | 22.14 ± 1.68 |
| 6 (n-butanol fraction of 40% Luo Han fruit powder) "Compound B" | >200 |

As shown in Table 1, Sample No. 7 showed strong activity against *P. falciparum* 7G8, with an $IC_{50}$ of 22.14 µg/ml. As shown in FIG. 1, Sample No. 7 Luo Han fruit extract demonstrated complete suppression of infected cell growth at higher concentrations as tested.

Example 1C

Parasite cultivation. Drug-sensitive clone 3D7 and multi-drug resistant (MDR) clone Dd2 of *Plasmodium falciparum*, obtained from the Malaria Research and Reference Reagent Resource Centre (MR4), Manassas, Va., USA, were maintained continuously in blood group O+ human erythrocytes and 10% human serum in a gas mixture consisting of 7% $CO_2$, 5% $O_2$ and 88% $N_2$.

The stock solutions of Example 1A, and CQ employed as the positive control (prepared as a 10 mM stock solution in PBS), were stored at −20° C. Each working solution was freshly prepared in cell culture medium. In all assays, the concentrations of DMSO and PBS were maintained at 0.5% which did not affect growth of control cultures.

In vitro inhibitory concentration assays. *P. falciparum* clones 3D7 and Dd2 were maintained continuously in blood group O+ human erythrocytes and 10% human serum in a gas mixture consisting of 7% $CO_2$, 5% $O_2$, and 88% $N_2$, synchronized by serial treatments with 5% D-sorbitol. In vitro growth inhibition of ring-stage-parasitized erythrocytes starting at 1% parasitemia and 2.5% hematocrit was determined by light microscopy of Giemsa-stained smears.

Figure 2:
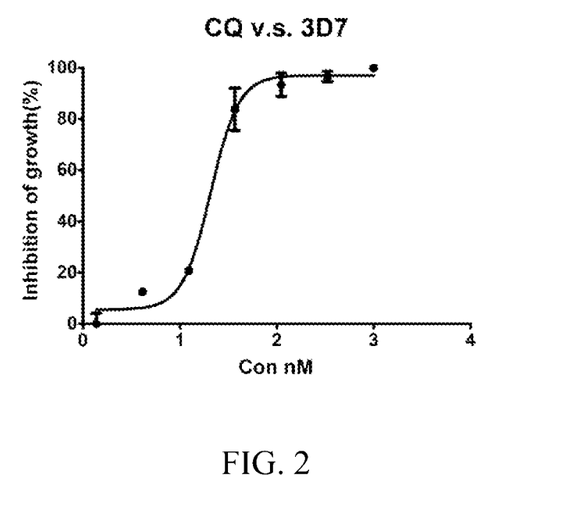
FIG. 2 depicts a dose-response curve (percent of growth inhibition vs. drug concentration) describing the effect of CQ on *P. falciparum* clones 3D7 in one embodiment as a drug-sensitive test strain.
Figure 3:
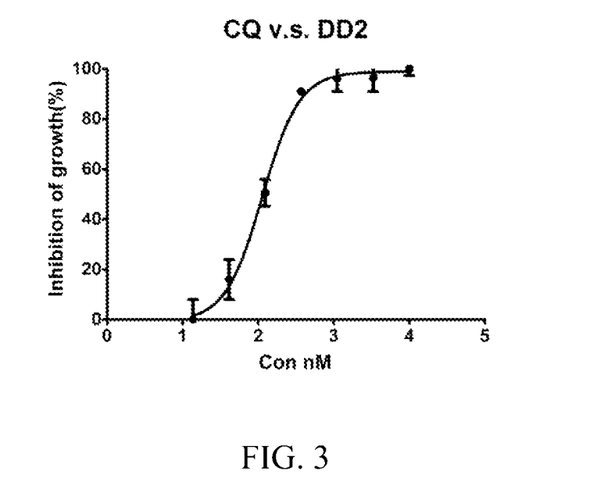
FIG. 3 depicts a dose-response curve (percent of growth inhibition vs. drug concentration) describing the effect of CQ on multi-drug resistant *P. falciparum* clones Dd2 in one embodiment as a drug-resistant test strain.

The results of the positive control experiments using CQ are presented in FIGS. 2 and 3.

FIG. 2 shows the effect of CQ on *P. falciparum* clones 3D7 in a dose response curve as percent of growth inhibition against drug concentration.

FIG. 3 shows the effect of CQ on *P. falciparum* clones Dd2 in a dose response curve as percent of growth inhibition against drug concentration.

Next, the extracts of Example 1A were tested based on the stock solutions discussed above. Table 2 below shows the effect of the extracts on *P. falciparum* clones 3D7 and Dd2.

TABLE 2

| | Percent of Inhibition (%, Mean ± SD) | |
| --- | --- | --- |
| Treatment Level | 3D7 | Dd2 |
| Sample No. 1 ($10^{-4}$ g/L) | 41.33 ± 0.00 | 56.14 ± 1.36 |
| Sample No. 2 ($10^{-4}$ g/L) | 41.87 ± 8.30 | 57.83 ± 2.39 |
| Sample No. 3 ($10^{-4}$ g/L) | 12.00 ± 11.31 | 44.58 ± 3.41 |
| Sample No. 4 ($10^{-4}$ g/L) | 25.33 ± 7.54 | 42.17 ± 0.00 |
| Sample No. 5 ($10^{-4}$ g/L) | 9.33 ± 7.54 | 50.12 ± 4.43 |
| Sample No. 6 ($10^{-4}$ g/L) | 4.00 ± 7.54 | 27.71 ± 6.82 |
| Sample No. 7 ($10^{-4}$ g/L) | 30.67 ± 7.54 | 42.17 ± 6.82 |
| Sample No. 8 ($10^{-4}$ g/L) | 9.33 ± 0.00 | 32.53 ± 6.82 |

The results of Table 2 clearly demonstrate that extracts derived from *Stevia* leaf and Luo Han fruit can inhibit the growth of *P. falciparum* clones 3D7 and Dd2. Furthermore, in reference to the extractive preparation of Example 1A yielding Samples 5-7, the results demonstrated that the active compounds appear to be in the EtOAc phase (Sample 7).

It is noteworthy that all of the extracts, whether derived from *Stevia* leaf or Luo Han fruit, demonstrated effectiveness to inhibit the malaria-causing parasite. In particular, the extracts, whether derived from *Stevia* leaf or Luo Han fruit, were highly effective against the drug-resistant strain Dd2.

Example 1D

The Luo Han Guo general extract (Sample 8) was prepared by extraction of dried Luo Han fruit with hot water as in Example 1A, and then fractionated with EtOAc and n-butanol respectively as in Example 1A to yield 3 fractions corresponding to Samples 5a-7a. Samples 6a-7a also correspond to "compound B" and "compound A" respectively.

The *P. falciparum* was cell synchronized by adding 5% of D-sorbitol, and synchronized cells were then spread on culture plates after achieving ring form phase, with an initial infection rate of 1% and PCV at 5%.

The DMSO stock solutions for Sample No. 7a ("Compound A") and Sample No. 6a ("Compound B") as above were diluted by culture medium to 2000 µg/ml as the mother solution and diluted by culture medium for gradient concentration in 3 fold serial dilution form in an activity testing assay (active ingredient solutions should be less than 10% of the culture system, and DMSO concentration should be lower than 0.5% to avoid adverse influence on *P. falciparum* growth). 10 µl active ingredient solution plus 90 µl *P. falciparum* culture medium were spread on each well. The cell culture was observed under microscope for infection rate by smear examination with the standard Giemsa stain.

Percent of inhibition=(infection rate of blank control−infection rate of active ingredient-treated or drug-treated group)/infection rate of blank control×100%.

Using a chloroquine and *Artemisinin* treated group as positive control, a dose response curve was generated as percent of growth value against active ingredient/drug concentration (Nonlinear Regression Analysis function in software Graphpad Prism 3.0, GraphPad Software, La Jolla, Calif., USA) in order to determine IC50 (half maximal inhibitory concentration). See Table 3 below.

Drug-sensitive (DS) clone 3D7 and multi-drug resistant (MDR) clone Dd2 of *Plasmodium falciparum*, obtained from the Malaria Research and Reference Reagent Resource Centre (MR4), Manassas, Va., USA, were maintained continuously in blood group O+ human erythrocytes and 10% human serum in a gas mixture consisting of 7% $CO_2$, 5% $O_2$ and 88% $N_2$.

In all assays, the concentrations of DMSO and PBS were maintained at 0.5% which did not affect growth of control cultures. In vitro inhibitory concentration assays. *P. falciparum* clones 3D7 and Dd2 were maintained continuously in blood group O+ human erythrocytes and 10% human serum in a gas mixture consisting of 7% CO2, 5% O2, and 88% N2, synchronized by serial treatments with 5% D-sorbitol. In vitro growth inhibition of ring-stage-parasitized erythrocytes starting at 1% parasitemia and 2.5% hematocrit was determined by light microscopy of Giemsa-stained smears.

TABLE 3

| | ($IC_{50}$, av. nM) | |
|---|---|---|
| Sample | 3D7 (DS) | Dd2 (MDR) |
| 1 | 219.56 ± 10.15 | 376.18 ± 12.39 |
| 2 | 231.87 ± 18.19 | 398.85 ± 22.31 |
| 3 | 222.98 ± 11.38 | 349.15 ± 13.76 |
| 4 | 528.76 ± 27.19 | 848.35 ± 40.67 |
| 5a | >1000 | >1000 |
| 6a "Compound B" | >1000 | >1000 |
| 7a "Compound A" | 90.89 ± 7.32 | 232.17 ± 16.76 |
| 8 | 457.32 ± 35.65 | 556.35 ± 49.98 |
| CQ (Chloroquine) | 1.37 ± 0.12 | 22.59 ± 0.82 |
| Coartem | 0.09 ± 0.00 | 0.13 ± 0.02 |

As shown in Table 3, Sample No. 7a contained the antimalarial activity after extraction. It was also found that Rebaudioside A (Sample 1) and Mogroside V (Sample 3) demonstrated generally comparable activities against the tested parasites.

Example 2

Checkerboard assay. The anti-malaria activity of Luohan fruit extracts and *Stevia* leaf extracts in vitro were determined and predicted using the malarial strain *P. falciparum* DD2. Samples are mixed into 1:2 series dilutions and the FIC index (FICI) is calculated. (Rand, K. H., Houck, H. J., Brown, P. et al. "Reproducibility of the microdilution checkerboard method for antibiotic synergy," Antimicrobial Agents & Chemotherapy (1993) 37:613-5; Eliopoulos, G. M., Moellering R. C. in *Antibiotics in Laboratory Medicine*, ed. Lorian V (Williams & Wilkins, Baltimore, Md., 1991), pp 432-492; Ghannoum, M. A., Fu, Y., Ibrahim, A. S., Mortara, L. A., Shafiq, M. C., Edwards, J. E., Jr., Criddle, R. S. Antimicrob. Agents Chemother. (1995) 39:2459-2465; Barchiesi, F., DiFrancesco, L. F., Scalise, G. "In Vitro Activities of Terbinafine in Combination With Fluconazole and Itraconazole Against Isolates of *Candida albicans* With Reduced Susceptibility to Azoles," Antimicrob. Agents Chemother. (1997) 41:1812-1814. Each of the foregoing references are incorporated herein by reference in their entirety.)

To determine whether the readout of the combination therapy is additive, synergistic, or indifferent, the FIC index (FICI) was calculated by the use of the checkerboard assay. The FICI represents the sum of the FICs of each drug tested, where the FIC (fractional inhibitory concentration) is determined for each drug by dividing the MIC of each drug when used in combination by the MIC of each drug when used alone. FICI=(MICdrug A in combination/MICdrug A alone)+(MICdrug B in combination/MICdrug B alone). The preassumptions are that (i) testing uses concentrations separated by a factor of 2, and (ii) one-dilution-step MIC changes are within the range of experimental error. Other sophisticated methods have also been used; for example, a contour surface-plot methodology was used in characterizing the nature of three antifungal agents in combinations using various concentrations of each agent.

The FICI demonstrates synergy at a value of ≤0.5, while values found in the range 0.5 to about 1.0 demonstrate an additive effect and not synergy.

Example 2A

Combination of *Stevia* leaf extract containing steviol glycosides and Luo Han fruit extract. A combination of Luo Han fruit extract (Compound A) as described above and a *Stevia* leaf extract containing steviol glycosides (as in Example 1A, Sample 2) provided an FICI of 0.3, demonstrating a synergistic ability to suppress growth of *P. falciparum* in vitro to a greater extent than either component alone. (MIC of compound A alone: 232 nM; MIC steviol glycosides alone: 400 nM; MIC compound A in combination: 14.5 nM; MIC steviol glycosides in combination: 100 nM).

Example 2B

Combination of *Stevia* leaf extracts containing steviol glycosides and mogroside V. In accordance with one embodiment, it is expected that a 1:1 wt/wt combination of a *Stevia* leaf extract containing steviol glycosides (as in Example 1A, Sample 2) and a Luo Han fruit pure extract powder containing Mogroside V (40%) (as in Example 1A, Sample 3) can suppress growth of *P. falciparum* in vitro and in vivo to a greater extent than either component alone.

Example 2C

Combination of rebaudioside A (Reb A) and mogroside V. In accordance with one embodiment, it is expected that a 1:1 wt/wt combination of Reb A (as in Example 1A, Sample 1) and a Luo Han fruit pure extract powder containing Mogroside V (40%) (as in Example 1A, Sample 3) can suppress growth of *P. falciparum* in vitro and in vivo to a greater extent than either component alone.

Example 2D

Combination of rebaudioside A (Reb A) and a Luo Han fruit extract. A combination of Reb A (as in Example 1A, Sample 1) and a Luo Han fruit extract (Compound A) provided an FICI of 0.3, demonstrating a synergistic ability to suppress growth of *P. falciparum* in vitro to a greater extent than either component alone. (MIC of compound A alone: 232 nM; MIC Reb A alone: 376 nM; MIC compound A in combination: 14.5 nM; MIC Reb A in combination: 94 nM).

Example 2E

Control

Combination of rebaudioside A (Reb A) and Artemsinin. A combination of Reb A (as in Example 1A, Sample 1) and artemsinin provided an FICI of about 0.9-1.0, demonstrating an additive effect only. (MIC of artemesinin alone: 0.13 nM;

MIC Reb A alone: 376 nM; MIC artemesinin in combination: 0.0081 nM; MIC Reb A in combination: 376 nM).

Example 3A

A composition including rebaudioside A (Reb A). In accordance with one embodiment, a patient (or each member of a patient cohort) is treated orally with one or more doses of an aqueous composition including a total daily dosage of up to about 500 mg rebaudioside A. It is expected that *P. falciparum* infection will be suppressed or inhibited within 3-7 days as assessed by standard blood film monitoring.

Example 3B

Combination of rebaudioside A (Reb A) and a Luo Han fruit extract containing mogroside V. In accordance with one embodiment, a patient (or each member of a patient cohort) is treated orally with one or more doses of an aqueous composition including a total daily dosage of up to about 500 mg rebaudioside A and up to about 500 mg mogroside V. It is expected that *P. falciparum* infection will be suppressed or inhibited within 3-7 days as assessed by standard blood film monitoring.

Example 4

In vitro antimalarial activity was also confirmed by a malaria SYBR Green I-based fluorescence method described previously by Smilkstein et al., Antimicrobial Agents and Chemotherapy, May 2004, p. 1803-1806, Vol. 48, No. 5, with slight modifications. Drug solutions were serially diluted with culture medium and distributed to asynchronous parasite cultures in 96-well plates in quadruplicate to achieve 0.2% parasitaemia with a 2% haematocrit in a total volume of 100 µL. The plates were then incubated for 72 h at 37° C. Following incubation, 100 µL of lysis buffer with 0.2 µL/mL SYBR Green 1 was added to each well. The plates were incubated at 37° C. for 1 h in the dark and then placed in a 96-well fluorescence plate reader (Multilabel HTS Counter; PerkinElmer, Waltham, Mass., USA) with excitation and emission wavelengths at 497 nm and 520 nm, respectively, for measurement of fluorescence. The 50% inhibitory concentration ($IC_{50}$) was determined by non-linear regression analysis of logistic dose—response curves using GraphPad Prism software (GraphPad Software Inc., La Jolla, Calif.). This example serves as a comparative method.

Next, the assay portion of procedure of Example 1C was performed using Coartem as a positive control. Coartem is a fixed-dose artemisinin-based combination therapy (ACT) available from Novartis AG, Basel, Switzerland. Each Coartem tablet contains 20 mg artemether and 120 mg lumefantrine. Artemether has a rapid onset of action and is rapidly eliminated, whereas lumefantrine is eliminated more slowly. Consequently, the combination rapidly clears parasites, while also preventing the reappearance of parasites in the blood. The drug has been widely used in China to replace chloroquine (CQ) for the treatment and prophylaxis of malaria. Table 4 shows the effect of standard drug treatments on *P. falciparum* clones 3D7 and Dd2 as determined by the fluorescence method. It is believed that the active compounds found in the previous examples would also provide significant if not comparable inhibition of parasitic cell growth.

TABLE 4

| Treatment | In vitro susceptibility ($IC_{50}$, nM) | |
| --- | --- | --- |
| | 3D7 | Dd2 |
| CQ | 1.63 ± 0.10 | 22.14 ± 1.96 |
| Coartem | 0.07 ± 0.09 | 0.09 ± 0.05 |

$IC_{50}$'s are presented as means ± standard errors of the means (n > 3).

The compositions of the present invention may be administered in combination with an acceptable carrier. The active ingredients in such formulations may comprise from 1% by weight to 99% by weight, or alternatively, 0.1% by weight to 99.9% by weight. An "acceptable carrier" means any carrier, diluent or excipient that is compatible with the other ingredients of the formulation and not deleterious to the user. Useful excipients include microcrystalline cellulose, magnesium stearate, calcium stearate, or any acceptable sugar (e.g., mannitol, xylitol).

The pharmaceutical compositions of the present invention may be administered in combination with a pharmaceutically acceptable carrier. The active ingredients in such formulations may comprise from 1% by weight to 99% by weight, or alternatively, 0.1% by weight to 99.9% by weight. "Pharmaceutically acceptable carrier" means any carrier, diluent or excipient that is compatible with the other ingredients of the formulation and not deleterious to the user.

The antimalarial compositions of the present invention and potent compounds derived from Luo Han fruit and/or *Stevia* leaf may be administered in combination with an acceptable carrier. The active ingredients in such formulations may comprise from 1% by weight to 99% by weight, or alternatively, 0.1% by weight to 99.9% by weight. An "acceptable carrier" means any carrier, diluent or excipient that is compatible with the other ingredients of the formulation and not deleterious to the user.

Delivery System

Suitable dosage forms include tablets, capsules, solutions, suspensions, powders, gums, and confectionaries. Sublingual delivery systems include, but are not limited to, dissolvable tabs under and on the tongue, liquid drops, and beverages. Edible films, hydrophilic polymers, oral dissolvable films or oral dissolvable strips can be used. Other useful delivery systems comprise oral or nasal sprays or inhalers, and the like.

For oral administration, the active compounds may be combined with one or more solid inactive ingredients for the preparation of tablets, capsules, pills, powders, granules or other suitable dosage forms. For example, the active agent may be combined with at least one excipient such as fillers, binders, humectants, disintegrating agents, solution retarders, absorption accelerators, wetting agents, absorbents, or lubricating agents. Other useful excipients include magnesium stearate, calcium stearate, mannitol, xylitol, sweeteners, starch, carboxymethylcellulose, microcrystalline cellulose, silica, gelatin, silicon dioxide, and the like.

Routes of Administration

The active compounds may be administered by any route, including but not limited to oral, sublingual, buccal, ocular, pulmonary, rectal, and parenteral administration, or as an oral or nasal spray (e.g. inhalation of nebulized vapors, droplets, or solid particles). Parenteral administration includes, for example, intravenous, intramuscular, intraarterial, intraperitoneal, intranasal, intravaginal, intravesical (e.g., to the bladder), intradermal, transdermal, topical, or subcutaneous administration. For example, the active ingredient may be localized in a depot for controlled release to the circulation.

The treatment may be carried out for as long a period as necessary, either in a single, uninterrupted session, or in discrete sessions. The treating physician will know how to increase, decrease, or interrupt treatment based on patient response. According to one embodiment, treatment is carried out for from about one day to about seven days. The treatment schedule may be repeated as required.

In conclusion, it has been shown that both purified Reb A and crude extracts of *Stevia* leaf are highly effective against known drug-resistant strains of the parasite that causes malaria. It has also been shown that both purified and crude extracts of Luo Han guo fruit are highly effective against known drug-resistant strains of the parasite that causes malaria. It is further expected that combinations of Reb A and Luo Han fruit extract would be highly effective against known drug-resistant strains of the parasite that causes malaria.

While in the foregoing specification this invention has been described in relation to certain embodiments thereof, and many details have been put forth for the purpose of illustration, it will be apparent to those skilled in the art that the invention is susceptible to additional embodiments and that certain of the details described herein can be varied considerably without departing from the basic principles of the invention.

As used in the specification and the appended claims, the singular forms of "a," "an" and "the" include plural references unless the context clearly dictates otherwise. For example, the term "a leaf" or "leaf" includes a plurality of leaves.

All references cited herein are incorporated by reference in their entirety. The present invention may be embodied in other specific forms without departing from the spirit or essential attributes thereof and, accordingly, reference should be made to the appended claims, rather than to the foregoing specification, as indicating the scope of the invention.

We claim:

1. A method of treating an individual having a malarial infection, comprising administering to the individual an effective amount of an antimalarial composition comprising a therapeutically effective amount of rebaudioside A, a therapeutically effective amount of a Luo Han fruit extract, a therapeutically effective amount of a compound selected from the group consisting of artemether, arteether, artesunate, and dihydroartemisinin, and an acceptable carrier, wherein the rebaudioside A and the Luo Han fruit extract are present in a 1:1 weight combination in a range between about 1% to 99% by weight of the total composition.

2. The method of claim 1, wherein the malarial infection is drug-resistant.

3. An antimalarial composition comprising a therapeutically effective amount of rebaudioside A, a therapeutically effective amount of a Luo Han fruit extract, a therapeutically effective amount of a compound selected from the group consisting of artemether, arteether, artesunate, and dihydroartemisinin, and an acceptable carrier, wherein the rebaudioside A and the Luo Han fruit extract are present in a 1:1 weight combination in a range between about 1% to 99% by weight of the total composition.

4. The antimalarial composition of claim 3, further comprising a therapeutically effective amount of a compound selected from the group consisting of mefloquine, halofantrine, artesunate, artemether, chloroquine, lumefantrine, primaquine, sulfadoxine, sulfalene, pyrimethamine, doxycycline, tetracycline, azithromycine, proguanil, cycloguanil, dapsone, artemsinin, atovoquone, and combinations thereof.

5. The antimalarial composition of claim 4, wherein the acceptable carrier is a pharmaceutically acceptable carrier.

6. The antimalarial composition of claim 4 formulated for oral, parenteral, intravenous, intramuscular, transdermal, buccal, subcutaneous, or suppository administration.

7. The antimalarial composition of claim 3, wherein the effective amount of rebaudioside A is in a range of about 10 mg to about 500 mg, and the effective amount of the Luo Han fruit extract is in a range of about 10 mg to about 500 mg.

8. The antimalarial composition of claim 3, formulated for oral, sublingual, buccal, intranasal, parenteral, intravenous, intradermal, transdermal, and subcutaneous administration.

9. The antimalarial composition of claim 3, wherein the carrier is an excipient selected from the group consisting of microcrystalline cellulose, magnesium stearate, calcium stearate, mannitol, and xylitol.

* * * * *